United States Patent
Ahn et al.

(10) Patent No.: US 11,191,610 B2
(45) Date of Patent: Dec. 7, 2021

(54) BIOPSY SITE MARKER WITH MICROSPHERE COATING

(71) Applicant: Devicor Medical Products, Inc., Cincinnati, OH (US)

(72) Inventors: Harry Ahn, Liberty Township, OH (US); Elijah Kreider, Hamilton, OH (US); Bryan R. Keller, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 447 days.

(21) Appl. No.: 16/141,077

(22) Filed: Sep. 25, 2018

(65) Prior Publication Data

US 2019/0090977 A1    Mar. 28, 2019

Related U.S. Application Data

(60) Provisional application No. 62/563,361, filed on Sep. 26, 2017.

(51) Int. Cl.
*A61B 90/00* (2016.01)
*A61B 17/00* (2006.01)
*B23P 15/00* (2006.01)

(52) U.S. Cl.
CPC .... *A61B 90/39* (2016.02); *A61B 2017/00526* (2013.01); *A61B 2017/00898* (2013.01); *A61B 2017/00942* (2013.01); *A61B 2090/3908* (2016.02); *A61B 2090/3925* (2016.02); *A61B 2090/3987* (2016.02); *A61M 2207/00* (2013.01); *B23P 15/00* (2013.01)

(58) Field of Classification Search
CPC .............. A61B 2090/3925; A61B 2090/3929
See application file for complete search history.

(56) References Cited

U.S. PATENT DOCUMENTS

| | | |
|---|---|---|
| 5,487,390 A | 1/1996 | Cohen et al. |
| 5,526,822 A | 6/1996 | Burbank et al. |
| 5,928,164 A | 7/1999 | Burbank et al. |
| 6,017,316 A | 1/2000 | Ritchart et al. |
| 6,086,544 A | 4/2000 | Hibner et al. |
| 6,083,524 A | 7/2000 | Sawhney et al. |
| 6,161,034 A | 12/2000 | Burbank et al. |

(Continued)

OTHER PUBLICATIONS

Ahmed, Enas M. "Hydrogel: Preparation, Characterization, and Applications: A Review." Journal of advanced research 6.2 (2015): 105-121.

(Continued)

*Primary Examiner* — Jason L Vaughan
(74) *Attorney, Agent, or Firm* — Frost Brown Todd LLC

(57) ABSTRACT

A marker delivery device including a delivery catheter, a marker, and a push rod. The delivery catheter is adapted to be inserted into a biopsy site and having a discharge opening. The marker having a coating layer disposed on the surface of a core. The coating layer includes an adhesive with a plurality of microbubbles. The microbubbles are configured to enhance visibility of the marker under ultrasound imaging. The marker is positioned inside the delivery catheter near the discharge opening. The push rod is positioned within the delivery catheter and is adapted to deploy the marker from the delivery catheter into the biopsy site.

17 Claims, 8 Drawing Sheets

(56) References Cited

U.S. PATENT DOCUMENTS

| | | | |
|---|---|---|---|
| 6,162,187 | A | 12/2000 | Buzzard et al. |
| 6,162,241 | A | 12/2000 | Coury et al. |
| 6,270,464 | B1 | 8/2001 | Fulton, III et al. |
| 6,347,241 | B2 | 2/2002 | Burbank et al. |
| 6,356,782 | B1 | 3/2002 | Sirimanne et al. |
| 6,427,081 | B1 | 7/2002 | Burbank et al. |
| 6,432,065 | B1 | 8/2002 | Burdorff et al. |
| 6,567,689 | B2 | 5/2003 | Burbank et al. |
| 6,605,294 | B2 | 8/2003 | Sawhney |
| 6,626,849 | B2 | 9/2003 | Huitema et al. |
| 6,662,041 | B2 | 12/2003 | Burbank et al. |
| 6,725,083 | B1 | 4/2004 | Burbank et al. |
| 6,752,768 | B2 | 6/2004 | Burdorff et al. |
| 6,790,185 | B1 | 9/2004 | Fisher et al. |
| 6,862,470 | B2 | 3/2005 | Burbank et al. |
| 6,993,375 | B2 | 1/2006 | Burbank et al. |
| 6,996,433 | B2 | 2/2006 | Burbank et al. |
| RE39,713 | E | 7/2007 | Sawhney et al. |
| 7,442,171 | B2 | 10/2008 | Stephens et al. |
| 7,565,191 | B2 | 7/2009 | Burbank et al. |
| 7,648,466 | B2 | 1/2010 | Stephens et al. |
| 7,651,505 | B2 | 1/2010 | Lubock et al. |
| 7,668,582 | B2 | 2/2010 | Sirimanne et al. |
| 7,792,569 | B2 | 9/2010 | Burbank et al. |
| 7,837,632 | B2 | 11/2010 | Stephens et al. |
| 7,854,706 | B2 | 12/2010 | Hibner |
| 7,877,133 | B2 | 1/2011 | Burbank et al. |
| 7,914,464 | B2 | 3/2011 | Burdorff et al. |
| 7,938,786 | B2 | 5/2011 | Ritchie et al. |
| 7,970,454 | B2 | 6/2011 | Jones et al. |
| 7,983,734 | B2 | 7/2011 | Jones et al. |
| 8,083,687 | B2 | 12/2011 | Parihar |
| 8,109,913 | B2 | 2/2012 | Dias et al. |
| 8,118,755 | B2 | 2/2012 | Hibner et al. |
| 8,177,792 | B2 | 5/2012 | Lubock et al. |
| 8,206,316 | B2 | 6/2012 | Hibner et al. |
| 8,219,182 | B2 | 7/2012 | Burbank et al. |
| 8,224,424 | B2 | 7/2012 | Burbank et al. |
| 8,241,226 | B2 | 8/2012 | Hibner et al. |
| 8,320,993 | B2 | 11/2012 | Sirimanne et al. |
| 8,361,082 | B2 | 1/2013 | Jones et al. |
| 8,447,386 | B2 | 5/2013 | Burbank et al. |
| 8,454,531 | B2 | 6/2013 | Speeg et al. |
| 8,498,693 | B2 | 7/2013 | Jones et al. |
| 8,600,481 | B2 | 12/2013 | Sirimanne et al. |
| 8,622,924 | B2 | 1/2014 | Speeg et al. |
| 8,626,269 | B2 | 1/2014 | Jones et al. |
| 8,626,270 | B2 | 1/2014 | Burbank et al. |
| 8,639,315 | B2 | 1/2014 | Burbank et al. |
| 8,702,623 | B2 | 4/2014 | Parihar et al. |
| 8,718,745 | B2 | 5/2014 | Burbank et al. |
| 8,764,680 | B2 | 7/2014 | Rhad et al. |
| 8,784,433 | B2 | 7/2014 | Lubock et al. |
| 8,801,742 | B2 | 8/2014 | Rhad et al. |
| 8,858,465 | B2 | 10/2014 | Fiebig |
| 8,880,154 | B2 | 11/2014 | Jones et al. |
| 8,938,285 | B2 | 1/2015 | Fiebig et al. |
| 8,939,910 | B2 | 1/2015 | Fisher |
| 8,965,486 | B2 | 2/2015 | Burbank et al. |
| 9,044,162 | B2 | 6/2015 | Jones et al. |
| 9,095,326 | B2 | 8/2015 | Ritchie et al. |
| 9,237,937 | B2 | 1/2016 | Burbank et al. |
| 9,326,755 | B2 | 5/2016 | Fiebig et al. |
| 9,327,061 | B2 | 5/2016 | Govil et al. |
| 9,345,457 | B2 | 5/2016 | Speeg et al. |
| 9,492,570 | B2 | 11/2016 | Sirimanne et al. |
| 9,649,093 | B2 | 5/2017 | Burbank et al. |
| 9,681,852 | B2 | 6/2017 | Vriezema et al. |
| 2005/0143650 | A1* | 6/2005 | Winkel .............. A61B 90/39 600/423 |
| 2006/0074345 | A1 | 4/2006 | Hibner |
| 2009/0131821 | A1 | 5/2009 | Speeg et al. |
| 2010/0152610 | A1 | 6/2010 | Parihar et al. |
| 2010/0160819 | A1 | 6/2010 | Parihar et al. |
| 2010/0234726 | A1* | 9/2010 | Sirimanne .......... A61K 49/006 600/426 |
| 2013/0324882 | A1 | 12/2013 | Mescher |
| 2014/0207000 | A1 | 7/2014 | Vriezema et al. |

OTHER PUBLICATIONS

Hahn, Markus et al., "Vacuum Assisted Breast Biopsy with Mammotome®," available Nov. 11, 2012, copyright 2013 by Devicor Medical Germany GmbH, published in Germany by Springer Medizin Verlag. 128 pages.

Klein, Rebecca L., et al. "Evaluation of a Hydrogel Based Breast Biopsy Marker (HydroMARK®) as an Alternative to Wire and Radioactive Seed Localization for Non-Palpable Breast Lesions." Journal of Surgical Oncology 105.6 (2012): 591-594.

Xu, Nan, et al. "Synthesis of Hollow Glass-Ceramics Microspheres via Template Method." Materials Research Bulletin 46.1 (2011): 92-97.

U.S. Appl. No. 61/566,793, filed Dec. 5, 2011.

International Search Report and Written Opinion dated Mar. 4, 2019 for Application No. PCT/US2018/052635, 13 pgs.

* cited by examiner

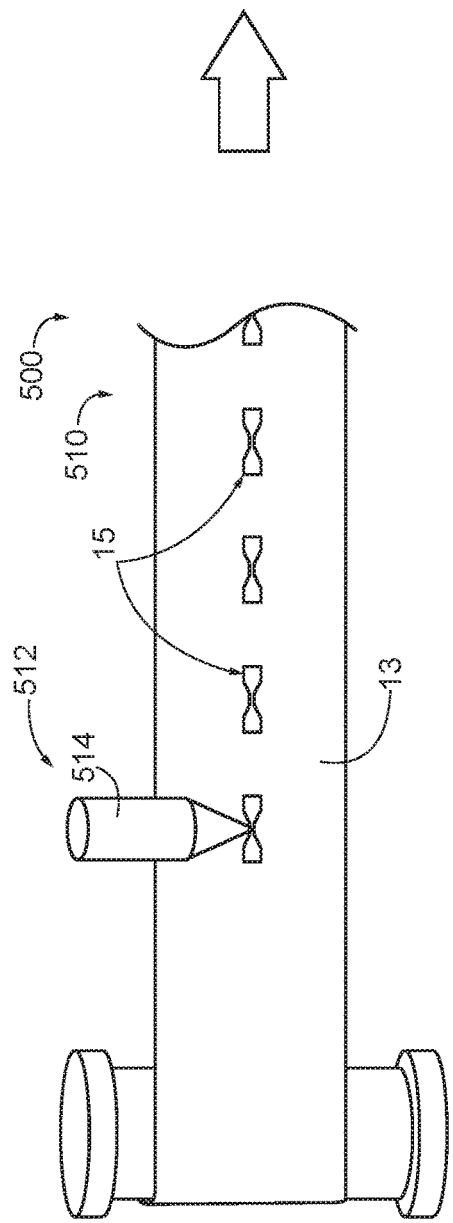
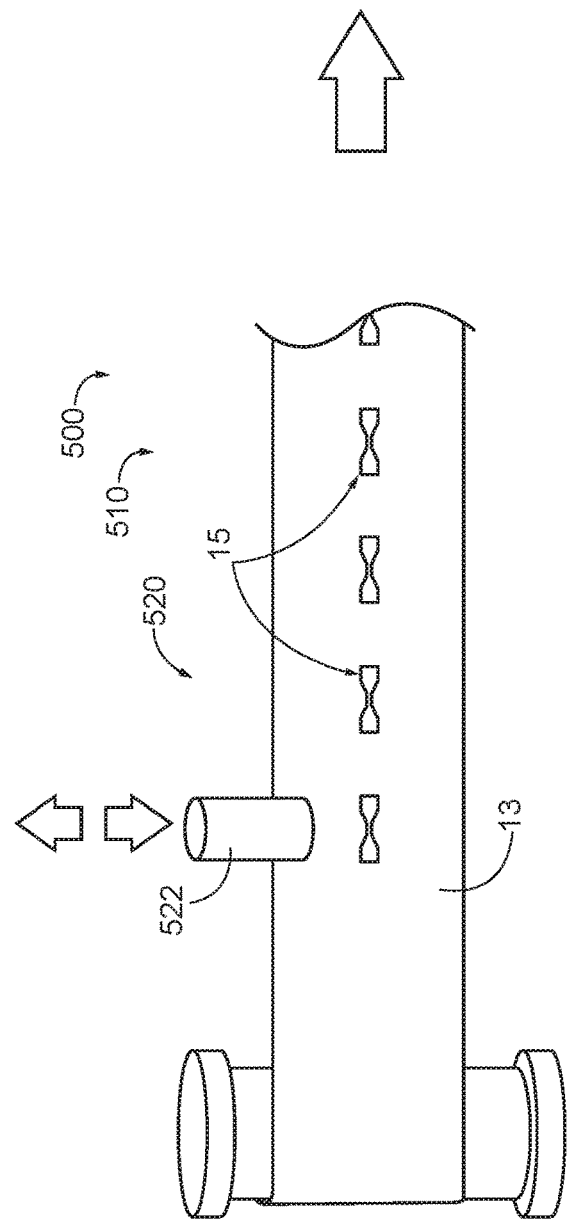

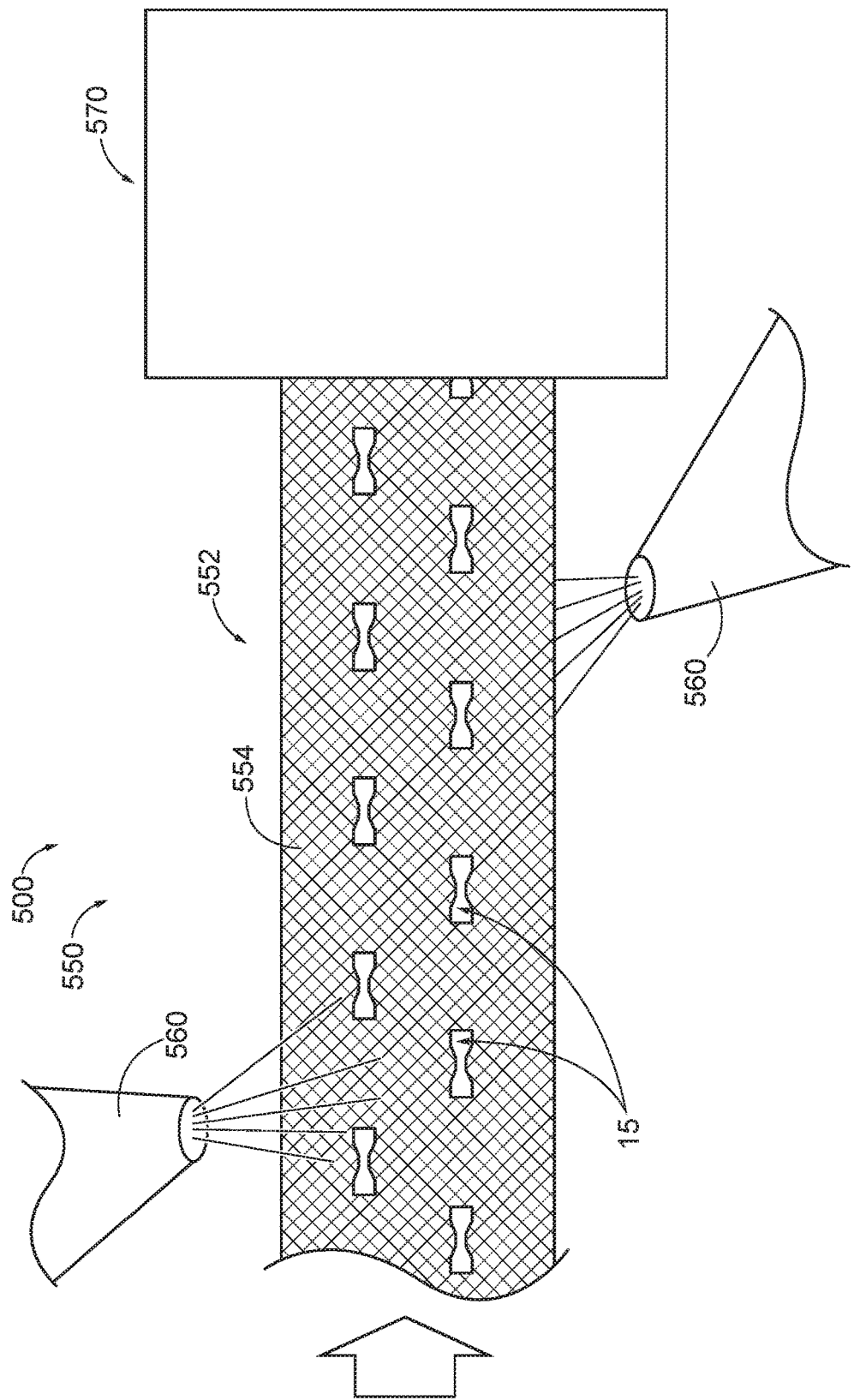

BIOPSY SITE MARKER WITH MICROSPHERE COATING

PRIORITY

This application claims priority to U.S. Provisional Patent App. No. 62/563,361 entitled "Biopsy Site Marker with Microsphere Coating," filed Sep. 26, 2017, the disclosure of which is incorporated by reference herein.

BACKGROUND

A number of patients will have breast biopsies because of irregular mammograms and palpable abnormalities. Biopsies can include surgical excisional biopsies and stereotactic and ultrasound guided needle breast biopsies. In the case of image directed biopsy, the radiologist or other physician may take a small sample of the irregular tissue for laboratory analysis. If the biopsy proves to be malignant, additional surgery (e.g., a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MRI) or x-ray may be used to locate the biopsy site. In order to assist the relocation of the biopsy site, a marker may be placed at the time of the biopsy.

The use of hydrogel materials for markers used after breast biopsies to mark the location where the biopsied tissue was removed is described in the following US Patents: U.S. Pat. No. 6,083,524, "Polymerizable biodegradable polymers including carbonate or dioxanone linkages," issued Jul. 4, 2000; U.S. Pat. No. 6,162,241, "Hemostatic tissue sealants," issued Dec. 4, 2000; U.S. Pat. No. 6,270,464, "Biopsy localization method and device," issued Aug. 7, 2001; U.S. Pat. No. 6,356,782, "Subcutaneous cavity marking device and method," issued Mar. 12, 2002; U.S. Pat. No. 6,605,294, "Methods of using in situ hydration of hydrogel articles for sealing or augmentation of tissue or vessels," issued Aug. 12, 2003; U.S. Pat. No. 8,600,481, "Subcutaneous cavity marking device," issued Dec. 3, 2013 and U.S. Pat. No. 8,939,910, "Method for enhancing ultrasound visibility of hyperechoic materials", issued Jan. 27, 2015. All of these US Patents are incorporated by reference in their entirety.

U.S. Pat. No. 8,939,910, "Method of Enhancing Ultrasound Visibility of Hyperechoic Materials," issued on Jan. 27, 2015, the contents of which having previously been incorporated herein by reference, describes a hydrogel marker that is enhanced by air cavities within the hydrogel that reflect under ultrasound imaging in different way than the reflection of the hydrogel, thereby making it easier to detect the hydrogel marker. Such air cavities in the enhanced hydrogel are hypoechoic and thus serve to further indicate the location of the marker. U.S. Pat. No. 8,939,910 gives an example of creating air cavities using inserts of differing sizes and shapes. The inserts are placed in the hydrogel during the manufacturing process and removed from the hydrogel after it is cured, leaving air-filled cavities in the hydrogel marker. The cavities are air-filled and reflecting differently under ultrasound imaging from the reflection of the hydrogel and making the hydrogel easier to detect under ultrasound.

In some contexts, a marker element is used to identify a biopsy site after a biopsy procedure. In some examples such marker elements are disposed within a bioabsorbable carrier. Regardless, it may be desirable to enhance the visibility of the marker element under ultrasonic visualization. One method of enhancing visualization of the marker element is to form the marker element of complex geometries that provide reflecting surfaces for ultrasonic radiation. However, these methods of enhancing visualization might not be completely satisfactory under all circumstances. Accordingly, in some contexts, it may be desirable to enhance a marker element by other means. While several systems and methods have been made and used for marking a biopsy site, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 6 depicts a perspective view of an exemplary continuous marker element forming and coating system for use in coating the element material of FIG. 2, the system including a laser formation stage;

FIG. 7 depicts a perspective view of an exemplary alternative continuous marker element forming and coating system of FIG. 6, the system including a stamp formation stage;

FIG. 8 depicts a perspective view of an element coating stage that may be readily used with either the laser formation stage of FIG. 6 or the stamp formation stage of FIG. 7;

Figure 1C:
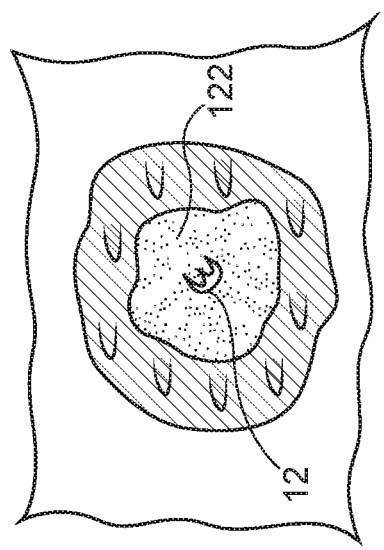
FIGS. 1A, 1B, and 1C show exemplary aspects of placement of a biopsy site marker, in accordance with aspects of the present disclosure.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It may be beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable for the marker to remain visible under ultrasound. It may also be desirable to make the marker readily identifiable relative to other structural features of a patient. For instance, it may be desirable for the marker to be distinguishable under ultrasound visualization from microcalcifications to avoid inadvertently characterizing the marker as a microcalcification during subsequent ultrasonic examinations. Generally, microcalcifications are used in the field to identify suspicious lesions or masses. Thus, it is generally desirable for the ultrasound view to be distinguishable as a marker and not inadvertently identified as a new mass.

I. EXEMPLARY MARKER

Figure 1B:
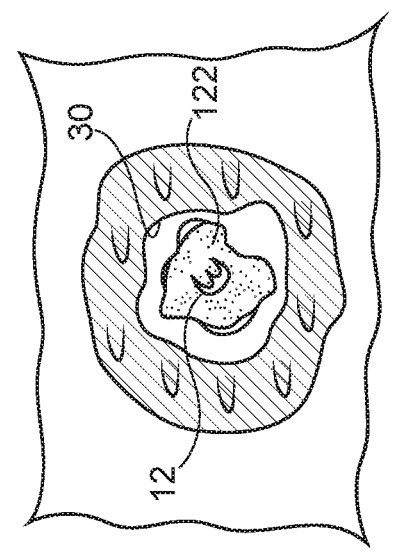
Figure 1A:
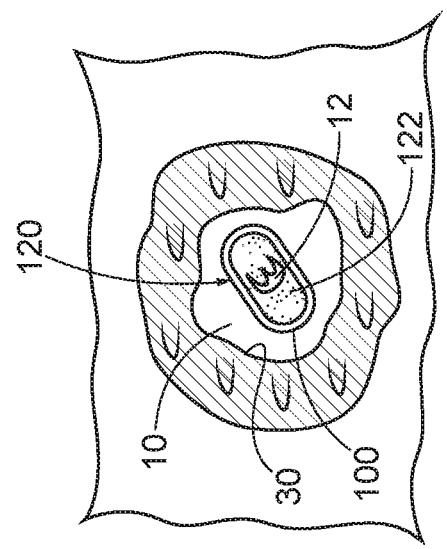

Aspects presented herein relate to devices and procedures for manufacturing a marker for percutaneously marking a biopsy cavity (10) having surrounding tissue (30), as shown in FIGS. 1A-1C. For instance, as seen in FIG. 1A, a marker (100) may be initially placed in the biopsy cavity (10) to facilitate relocation of the biopsy site. Marker (100) may comprise a carrier (120) and a marker element (12). Carrier (120) generally includes a bioabsorbable marker material (122). Thus, carrier (120) is generally configured for absorption into a patient after placement of marker (100) within the biopsy cavity (10). In some examples, carrier (120) can include a plurality of microbubbles to enhance visualization of carrier (120) under ultrasound. As will be described in greater detail below, such bubbles may be generally desirable to provide enhanced reflection of ultrasonic radiation from the interior and exterior of marker (100). As will be described in greater detail below, marker material (122) is generally bioabsorbable such that marker material (122) may be generally absorbed into the patient's tissue over time. In the present example, marker material (122) comprises a hydrogel that is initially in a dehydrated state. Although a hydrogel is used in the present example, it should be understood that in other examples marker material (122) may comprise other known bioabsorbable materials.

In the present example, marker (100) further includes a marker element (12) that is generally not bioabsorbable. Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other examples, marker (100) may be formed without a marker element (12). In still other examples, marker (100) may be formed with only marker element (12) such that carrier (120) is omitted and marker element (12) is in a "bare" form. In other words, in some examples marker (100) is formed of only carrier (120) as a bare clip.

Marker material (122) is generally expandable once disposed within a patient at a biopsy site. As shown in FIGS. 1B and 1C, the initially dehydrated marker material (122) may absorb fluid from the surrounding tissue (30) into which it is inserted. In response to this absorption of fluid, maker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured and the natural mechanical parameters of the tissue are substantially restored to those of the pre-damaged condition.

Marker (100) may be inserted into the body either surgically via an opening in the body cavity (30), or through a minimally invasive procedure using such devices as a catheter, introducer or similar type insertion device. Marker (100) may be delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via marker (100).

Marker (100) of the present example is large enough to be readily visible to a clinician under x-ray or ultrasonic viewing, for example; yet small enough to be able to be percutaneously deployed into the biopsy cavity and to not cause any difficulties with the patient. Although examples are described in connection with treatment and diagnosis of breast tissue, aspects presented herein may be used for markers in any internal, tissue, e.g., in breast tissue, lung tissue, prostate tissue, lymph gland tissue, etc.

Many properties of a marker, marker material and/or marker element may affect the intensity of its ultrasound reflection, including density, physical structure, molecular material, and shape. For example, sharp edges, or multiple reflecting surfaces on or within an object differing in density from its surroundings may enhance a marker's ability to be detected by ultrasound. Interfaces separating materials of different densities, such as between a solid and a gas, may produce strong ultrasound signals.

A typical human breast has a substantial number of features that are visualized with ultrasound. These features all have characteristic signals. Fibrous tissue or ligaments may tend to show up as bright streaks, fat may seem to appear as a dark gray area, the glandular tissue may appear as a mottled medium gray mass. Cancerous lesions may appear as a darker area with a rough outer edge that has reduced through transmission of the ultrasound energy.

However, due to the large amount of fibrous tissue normally present in a human breast, and due to the presence of ligaments running through the breast, a marker, carriers, and/or marker element that simply has a bright signal alone may not provide a useful signal that is readily discernable from the many anatomic features normally present within a human breast. Such markers, carriers, and/or marker elements may be small, being sized to fit within a syringe or other delivery tube, and so may not be readily distinguishable from natural features of the breast, which may include occasional small ultrasound-bright spots. Thus, it may be desirable for an ultrasound-detectable biopsy marker, carrier, and/or marker element to provide an ultrasound signal that can be readily differentiated from anatomic structures within the breast, so that the identification and marking of a biopsy cavity does not require extensive training and experience.

A permanent metal or hard plastic, such as a permanent, biocompatible plastic, or other suitable permanent marker may be left at a biopsy site at the completion of a biopsy if the site is to be located again in the future. Suture and collagen-based markers may not be considered ideal materials for use as markers because they are hyperechoic, i.e., difficult to see under ultrasound, because such materials are easily confused with other shadowing normal structures in the body such as fibrous tissue, fatty tissue, ducts in breast tissue, and the like, for example. Such tissue provides a background clutter that may mask the presence of a marker made of metal, hard plastic, or other hyperechoic material.

Water, unlike metal, hard plastic, and other hyperechoic materials, is hypoechoic, i.e., easy to see under imaging techniques such as ultrasound. Therefore, it can be advantageous if a marker made of a hyperechoic material such as metal or hard plastic could be surrounded by an easily seen quantity of water. A hydrogel that has absorbed fluid from surrounding tissue may provide such desirable ultrasound characteristics. The marker would become hydrated by natural body moisture after being positioned at a biopsy site, thereby surrounding the permanent marker with water. The water would be easily seen under ultrasound and therefore the permanent marker it surrounds would be easy to see.

The hydration of the marker material (122) of carrier (120) by the natural moisture of the tissue surrounding it causes expansion of the polymer and thus minimizes the risk of migration. The growing hydrogel based marker material (122) centers marker (100) in the biopsy cavity as it grows. As the hydrogel expands, naturally-present moisture from the surrounding tissue, the hydration enables increasing sound through transmission, appears more and more hypoechoic and is easy to visualize on follow up ultrasound studies.

The hydrated hydrogel marker material (122) of carrier (120) may also be used to frame permanent marker (12). The hypoechoic nature of the hydrated marker material (122) enables ultrasound visibility of the permanent marker (12) within the hydrogel hydrated marker material (122) because the permanent marker (12) is outlined as a specular reflector within a hypoechoic hydrated marker having a water-like nonreflective substrate.

Although marker (100) is described above as including both a bioabsorbable carrier (120) and a non-bioabsorbale marker element (12), it should be understood that in some examples carrier (120) may be omitted entirely. This in some examples, marker (100) comprises only marker element (12).

II. EXEMPLARY METHODS FOR MANUFACTURING ECHOGENIC COATING ON MARKER ELEMENT

In some contexts, marker elements similar to marker element (12) described above may be used to identify a biopsy site under ultrasonic visualization. This procedure may be used where a marker elements are deployed in a "bare" condition—or without a carrier similar to carrier (120) described above. However, ultrasonic visualization may also be used to visualize a marker element in contexts where a carrier is used, but after the carrier has dissolved into surrounding tissue. Accordingly, in some contexts it may be desirable to enhance visibility of a marker element similar to marker element (12) described above under ultrasonic visualization.

Marker elements similar to marker element (12) described above may be enhanced in a variety of ways. For instance, in some examples a marker element may include a plurality of obliquely oriented geometric features that may provide a plurality of projection surfaces for ultrasonic radiation regardless of the positioning of the marker element relative to the source of the ultrasonic radiation. While these methods of enhancement and other similar methods of enhancement may enhance visualization of a marker element under ultrasound in some circumstances, visibility may still be undesirable in some circumstances. For instance, when a marker element is not oriented directly perpendicular relative to the direction of propagation of ultrasonic radiation, visualization may be especially difficult. Thus, it may be desirable to use additional methods and/or features to enhance visualization of a marker element similar to marker element (12) described above.

One method of enhancing a marker element similar to marker element (12) described above is to coat the marker element with a coating of microspheres. Once such microspheres are applied to the surface of a marker element, each microsphere provides at least one surface that is always normal relative to the direction of propagation of ultrasonic radiation. Thus, ultrasonic visualization of a marker element can be substantially enhanced via a microsphere coating. Various systems and methods of coating a marker element with a variety of microspheres are described below. Although the systems and methods described below are discussed as generally discrete systems and methods, it should be understood that various steps and/or features of each system and/or method may be readily combined with steps and/or features of other systems and/or methods. Moreover, while each system and method described below includes discussion of several steps and/or features, it should be understood that in other systems and/or methods additional steps and/or features may be added as will be apparent to those of ordinary skill in the art in view of the teachings herein.

A. Exemplary Continuous Dip Coating System

Figure 2:
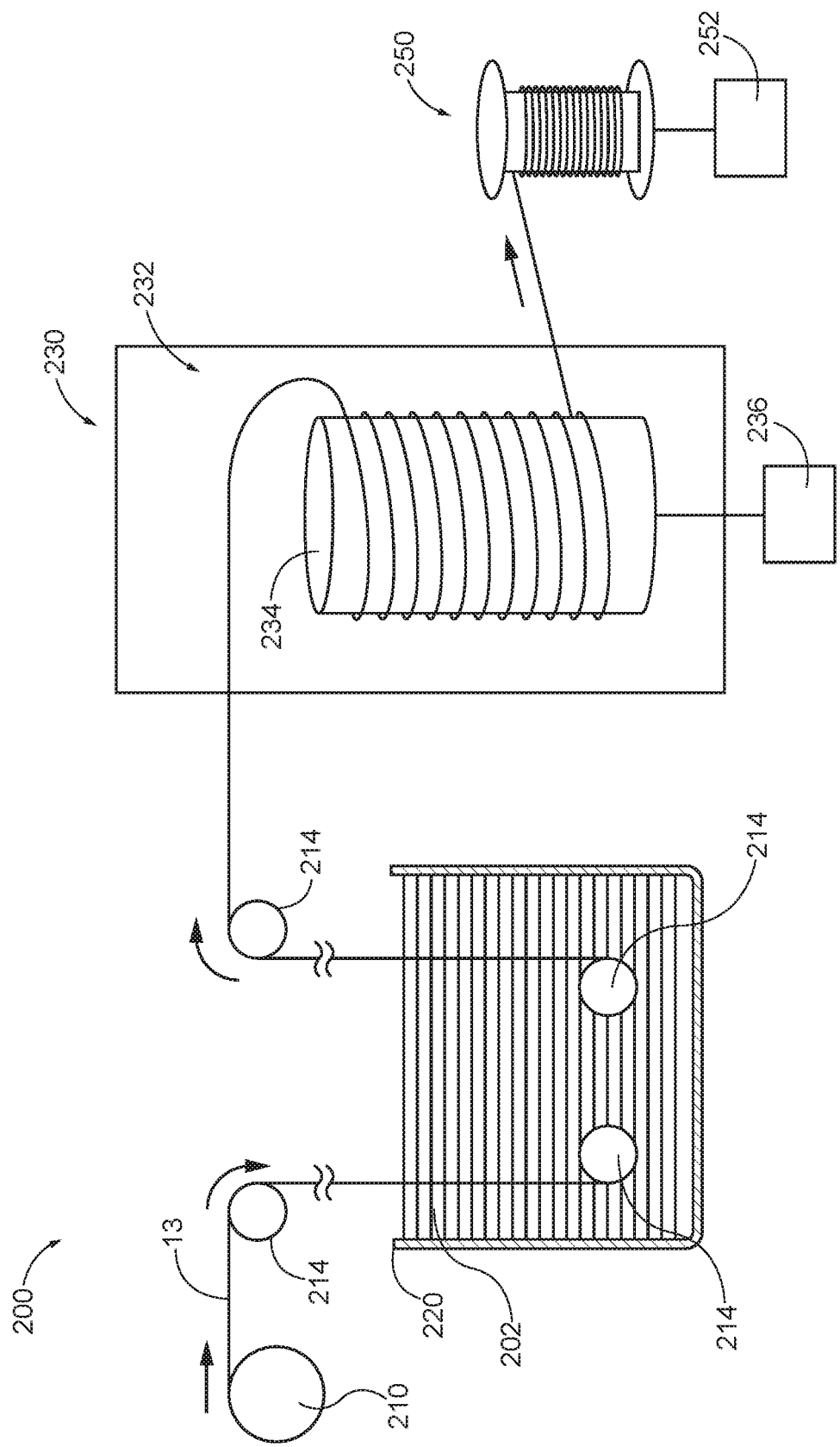
FIG. 2 depicts a side elevational view of an exemplary continuous dip coating system for use in coating an element material of the biopsy site marker of FIGS. 1A, 1B, and 1C.

FIG. 2 shows an exemplary continuous dip coating system (200) for use in an operation to coat an element material (13) with a coating material (202). Element material (13) is generally in wire or strip form (e.g., elongate thin strip of material) and includes any material suitable for forming a marker element such as marker element (12) described above. By way of example only, suitable materials can include various metals or metal alloys, hard plastics, or other radiopaque or hyperechoic materials known to those of ordinary skill in the art in view of the teachings herein.

Coating material (202) generally includes a plurality of microspheres suspended in a polymeric adhesive solution. Each microsphere generally includes a polymeric hollow exterior filled with a gas. In some examples a suitable gas filled microsphere is formed using at least some of the teachings of U.S. Pat. No. 5,487,390, entitled "Gas Filled Polymeric Microbubbles for Ultrasound Imaging," issued on Jan. 30, 1996, the teachings of which are incorporated by reference herein. The hard-polymeric exterior of each microsphere generally defines a spherical shape. Within the hollow interior of each microsphere can be filled with a variety of gasses. For instance, in some examples, suitable gasses may include atmospheric air, carbon dioxide, argon, and/or etc.

The diameter of each microsphere is generally less than 500 microns in the present example. The particular diameter of each microsphere is generally related to the frequency and wavelength ranges used for ultrasonic visualization. For instance, commercially available transducers used for ultrasonic visualization may generally produce frequencies in the range of 2 to 8 MHz. Correspondingly, wavelengths generally range from 2500 µm to 7700 µm. Because the diameter of each microsphere should generally be several times smaller than the wavelength of the ultrasonic radiation, a suitable microsphere diameter is generally less than 1000 µm. By way of example only, each microsphere can have a diameter of about 0.1 µm to 500 µm (average), more particularly 1 µm to 250 µm (average), and most particularly 1 µm to 100 µm (average). Manufacturing of suitable microspheres may be performed in accordance with at least some of the teachings of N. Xu, J. Dai, J. Tian, X. Ao, L. Shi, X. Huang, and Z. Zhu, *Mater. Res. Bull.*, 2011, 46:92, the teachings of which are incorporated by reference herein.

The adhesive solution of coating material (202) can include a plurality of polymeric adhesive solutions. For instance, in some examples the adhesive solution includes a solution of 15 wt. % poly(N-vinyl-pyrrolidone)-co-poly (butyl acrylate) in ethanol. In other examples, the adhesive solution includes polyurethanes, polyethylene, polypropylene, poly(ethylene-co-vinyl acetate) including partially hydrolyzed poly(ethylene-co-vinyl acetate), poly(ethylene-co-vinyl alcohol), polysilicones, polybutylene and isomeric polybutylene such as polyisobutylene, polyisoprene, halogenated rubbers, halogenated elastomers such as polyvinyl chloride, polymers and copolymers of vinyl-alkylenes, polymeric ethylene oxides, polyethers, polyacrylates such as poly(hydroxyethyl acrylate), paints such as Chemglaze A276, S13GLO, YB-71, and D-11, which are the paints used on the United States space shuttle, polyepoxides such as polymers of glycidol, polyacrylamides, polypeptides, polyvinylpyrrolidone, gelatin and/or etc.

In some examples, it may be desirable for the ultimate coating provided by coating material (202) to be more flexible. For instance, when a coating process includes a coiling operation, more flexibility in the final coating may be desired to reduce flaking or chipping of the coating as element material (13) is manipulated in the coated condition. In such circumstances, the adhesive solution of coating material (202) can include poly(N-vinyl-pirrolidone, poly (N-vinyl-pirrolidone-co-butylacrylate), poly(-vinyl pyridine), polyacrylamides, e.g. poly(N-isopropylacrylamide), poly(amido-amines), poly(ethylene imine), poly(ethylene oxide-block-propylene oxide), poly(ethylene oxide-block-propylene oxide-block-ethylene oxide), poly(styrene-block-isobutylene-block-styrene), poly(hydroxystyrene-block-isobutylene-block-hydroxystyrene), polydialkylsiloxanes, polysaccharides, polyacrylates and polyalkylmethacrylates, e.g., polymethylmethacrylate and poly(2-hydroxyethylmethacrylate).

As seen in FIG. 2, coating system (200) includes a raw material spool (210), a plurality of manipulation rolls (214), a dip tank (220), a drying assembly (230), and a coat spool (250). Raw material spool (210) is configured to hold a predetermined length of element material (13) in a spooled configuration. As will be described in greater detail below, raw material spool (210) is generally configured to rotate to continuously feed uncoated element material (13) towards other components of coating system (200). In some examples, raw material spool (210) is mounted on one or more bearings, rollers, and/or other rotational features to promote rotation of raw material spool (210) as element material (13) is fed toward other components of coating system (200). Although not shown, it should be understood that raw material spool (210) can be associated with motors or other drivers to drive rotation of raw material spool (210) and thereby "push" element material (13) toward other components of coating system (200). Of course, such features are merely optional as some components of coating system can be configured to "pull" element material (13) away from raw material spool (210).

Dip tank (220) is generally configured to hold a predetermined quantity of coating material (202). As can be seen, dip tank (220) generally defines a rectangular or square shape, although numerous alternative shapes may be used. Dip tank (220) is positioned ahead of raw material spool (210) such that element material (13) from raw material spool (210) and into dip tank (220). As will be described in greater detail below, this configuration permits element material (13) to be fully submerged into coating material (202) for a complete coating of element material (13) as element material (13) travels through dip tank (220).

A plurality of manipulation rolls (214) are positioned both adjacent to and within dip tank (220). Each manipulation roll (214) is generally configured to rotate freely such that element material (13) can slide relative to each manipulation roll (214) relatively free from friction. In addition, each manipulation roll (214) is fixed in a static position relative to dip dank (220), thereby permitting each manipulation roll (214) to alter the direction of element material (13) as element material (13) slides past a given manipulation roll (214). The particular configuration of each manipulation roll (214) is configured to direct element material (13) away from raw material spool (210), into dip tank (220), out of dip tank (220), and onto other components of coating system (200).

In the present example, a set of manipulation rolls (214) is positioned above dip tank (220) and a set of manipulation rolls (214) are positioned within dip tank (220). Thus, manipulation rolls (214) form a generally square or rectangular pattern. Although the present example is shown as including four manipulation rolls (214) in a generally square configuration, it should be understood that any other suitable number and any other suitable configuration may be used. For instance, in some examples three manipulation rolls (214) may be used with two outside of dip tank (220) and one within dip tank (220). In addition, although not shown, additional manipulation rolls (214) of varying diameters may be positioned at several positions along element material (13) to further manipulate element material (13) or otherwise stabilize element material (13) as element material (13) moves through coating system (200).

Drying assembly (230) comprises a drying chamber (232), and a cylindrical drum roll (234). Drying chamber (232) is configured to accommodate drum roll (234) such that drum roll (234) may freely rotate within drying chamber (232). Although not shown, it should be understood that in some examples drying chamber (232) is in communication with blowers, heaters, light emitters, or other devices configured to manipulate the conditions within drying chamber (232). As will be described in greater detail below, the air or other conditions within drying chamber (232) are generally manipulated to accelerate drying and/or curing of coating material (202) as element material (13) passes through drying assembly (230).

Drum roll (234) is configured to manipulate element material (13) through drying chamber (232). As described above, drying chamber (232) the air and/or conditions within drying chamber (232) are generally manipulated to accelerate drying and/or curing of coating material (202). To increase the amount of exposure of coating material (202) to the conditions of drying chamber (232), drum roll (234) defines an axial length that is configured to accommodate several turns of element material (13) in a helical configuration. Although not shown, it should be understood that in some examples drum roll (234) can include channels, protrusions, and/or other geometric features to direct element material (13) along the helical path shown in FIG. 2.

At least a portion of drum roll (234) is in mechanical communication with a motor (236). Motor (236) is configured to drive rotation of drum roll (234) to thereby "pull" element material (13) through drying assembly (230). In some example, the rotation generated by motor (236) may also be sufficient to "pull" element material (13) from raw material spool (210) through dip tank (220) and into drying assembly (230).

Coat spool (250) is positioned next to drying assembly (230). Coat spool (250) is generally configured to rotate to accumulate coated element material (13) after element material (13) passes through drying assembly (230). To assist with such rotation, coat spool (250) is mechanically coupled to a motor (252), which provides rotation of coat spool (250). In some examples, motor (252) provides sufficient power to coat spool (250) to merely "pull" element material (13) from drying assembly (230) to coat spool (250). However, in other examples, motor (252) provides sufficient power to "pull" element material (13) entirely through coating system (200). In such versions, drum roll (234) may act as an idler and motor (236) may be omitted.

In an exemplary method of coating element material (13) using coating system (200), element material (13) begins at raw material spool (210). It should be understood that at this stage a predetermined amount of element material (13) is spooled around raw material spool (210) to continuously provide element material (13) as raw material spool (210) is rotated. To drive element material (13) through the components of coating system (200), coat spool (250) is positioned at an end of coating system (200) opposite of raw material spool (210). Motor (252) thus drives rotation of coat spool (250) to "pull" element material (13) from raw material spool (210) to coat spool (250).

As element material (13) progresses between raw material spool (210) and coat spool (250), element material (13) is first directed into dip tank (220) via manipulation rolls (214). This submerges element material (13) in coating material (202), thereby fully coating the exterior of element material (13) with coating material (202). Prior to beginning the coating process, it should be understood that coating material (202) may be manufactured in accordance with the specifications above and then added to dip tank (220) initially or on a continuous basis.

Once element material (13) has been coated via dip tank (220), manipulation rolls (214) manipulate the coated element material (13) out of dip tank (220) and toward dying assembly (230). Element material (13) is then received in drying assembly (230) to initiate the drying process.

During the drying process, element material (13) winds around drum roll (234) in a helical configuration. Drum roll (234) is rotated via motor (236) to progressively drive element material (13) lower on drum roll (234). This process exposes element material (13) to the conditions of drying chamber (232), which accelerates the drying and/or curing of coating material (202) on element material (13). In the present example, the process of moving element material (13) from the top of drum roll (234) to the bottom of drum roll (234) takes between about 30 minutes to about 3 hours (e.g., exposure time). However, in other examples the speed of drum roll (234) or the physical dimensions of drum roll (234) can be varied to increase or decrease the particular amount of exposure time.

As described above, exposure to the conditions within drying chamber (232) accelerates drying and/or curing of coating material (202) on element material (13). In the present example, this includes heating the atmospheric temperature of drying chamber (232) to approximately 100° C. In other examples, this can also include increasing the movement of air within drying chamber (232) to a predetermined velocity. In still other examples, coating material (202) may not be completely responsive to heat. In such examples, various alternative drying and/or curing mechanisms may be used. For instance, in some examples coating material (202) is cured by certain wavelengths of light. Thus, coating material (202) and element material (13) can also be exposed to certain predetermined wavelengths of light when disposed within drying chamber (232).

After element material (13) progresses to the bottom of drum roll (234), element material (13) travels to coat spool (250). Once at coat spool (250), element material (13) is wound around coat spool (250) for storage until all element material (13) has progressed from raw material spool (210) to coat spool (250).

After element material (13) has progressed entirely from raw material spool (210) to coat spool (250), element material (13) is entirely coated with coating material (202). Element material (13) is next used to prepare a marker element similar to marker element (12) described above. The particular marker element formed depends in part on the initial shape of element material (13). For instance, if element material (13) is in wire form, element material (13) can be cut into a plurality of segments of a predetermined length. Each segment is then shaped to form a predetermined marker element geometry such as a spring shape. Alternatively, if element material (13) is in a strip form, element material (13) can be cut into a plurality of blanks of a predetermined shape (e.g., bow tie). Each blank can then be shaped into a final configuration as desired.

Regardless of the particular formation of marker material (13) into a marker element, each completed marker element is next formed into a completed marker similar to marker (100) described above. As described above, the marker element may be used alone as the marker (e.g., a bare marker) or suspended in a carrier similar to carrier (120) described above. Regardless, the final marker can be next used for marking purposes by inserting the completed marker into tissue via a marker delivery device or other suitable devices and/or methods as will be described in greater detail below.

B. Exemplary Continuous Spray Coating System

Figure 3:
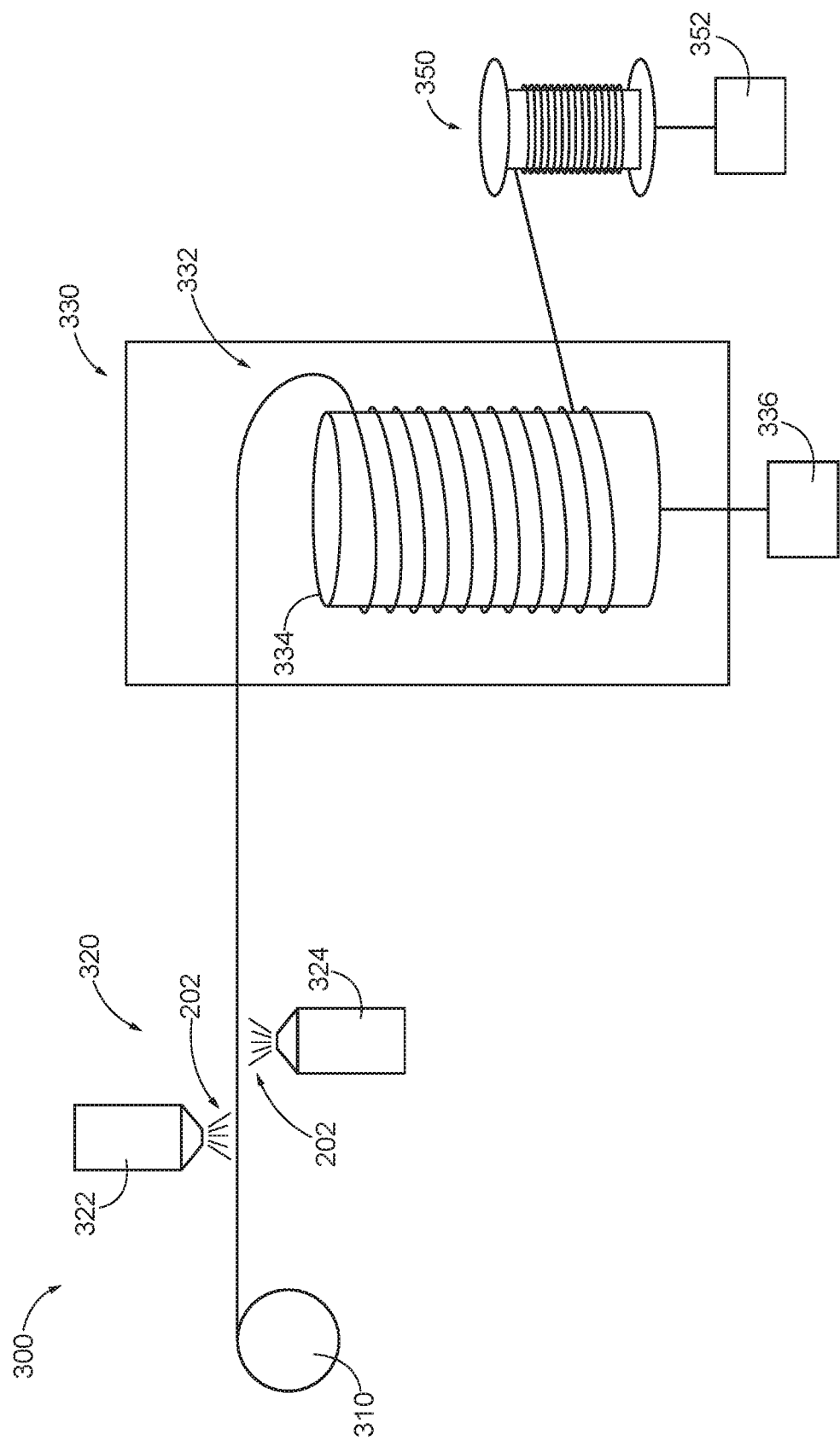
FIG. 3 depicts a side elevational view of an exemplary continuous spray coating system for use in coating the element material of FIG. 2.

FIG. 3 shows an exemplary continuous spray coating system (300) for use in an operation to coat element material (13) with coating material (202). Coating system (300) is substantially similar to coating system (200) described above, except as otherwise described herein. For instance, like with coating system (200), coating system (300) includes a raw material spool (310), a drying assembly (330), and a coat spool (350). However, unlike coating system (200), coating system (300) omits a structure similar to dip tank (220). Instead, coating system (300) includes a spray assembly (320), which is used to coat element material (13) with coating material (202) as element material (13) is fed from raw material spool (310) to coat spool (350).

Raw material spool (310) is substantially the same as raw material spool (210) described above. For instance, raw material spool (310) is configured to hold a predetermined length of element material (13) in a spooled configuration. As will be described in greater detail below, raw material spool (310) is generally configured to rotate to continuously feed uncoated element material (13) toward other components of coating system (300). In some examples, raw material spool (310) is mounted on one or more bearings, rollers, and/or other rotational features to promote rotation of raw material spool (310) as element material (13) is fed towards other components of coating system (300). Although not shown, it should be understood that raw material spool (310) can be associated with motors or other drivers to drive rotation of raw material spool (310) and thereby "push" element material (13) toward other components of coating system (300). Of course, such features are merely optional as some components of coating system can be configured to "pull" element material (13) away from raw material spool (310).

Spray assembly (320) is disposed between raw material spool (310) and drying assembly (330). Spray assembly (320) includes a plurality of sprayers (322, 324) oriented in various positions around element material (13). In the present example, spray assembly (320) includes an upper sprayer (322) and a lower sprayer (324). In this configuration, upper sprayer (322) is configured to spray coating material (202) on an upper surface of element material (13). Similarly, lower sprayer (324) is configured to spray coating material (202) on a lower surface of element material (13). Thus, sprayers (322, 324) together are configured to spray element material (13) with coating material (202) to fully coat every surface of element material (13). While each sprayer (322, 324) is characterized in the present example as being in either an upper position or a lower position, it should be understood that no such configuration is required. For instance, in some examples each sprayer (322, 324) may be placed at the sides of element material (13) or in a variety of positions around the perimeter of element material (13). In addition, or in the alternative, in other examples more than two sprayers (322, 324) may be used, with each spray positioned in a variety of suitable positions as will be apparent to those of ordinary skill in the art in view of the teachings herein.

Although not shown, it should be understood that spray assembly (320) can include a one or more manipulation rolls similar to manipulation rolls (214) described above. For instance, in some examples, a manipulation roll can be positioned both adjacent to each sprayer (322, 324) to stabilize element material (13) as element material (13) passes through spray assembly (320). In addition, although not shown, additional manipulation rolls of varying diameters may be positioned at several positions along element material (13) to further manipulate element material (13) or otherwise stabilize element material (13) as element material (13) moves through coating system (200).

Drying assembly (330) comprises a drying chamber (332), and a cylindrical drum roll (334). Drying chamber (332) is configured to accommodate drum roll (334) such that drum roll (334) may freely rotate within drying chamber (332). Although not shown, it should be understood that in some examples drying chamber (332) is in communication with blowers, heaters, light emitters, or other devices configured to manipulate the conditions within drying chamber (332). As will be described in greater detail below, the air or other conditions within drying chamber (332) are generally manipulated to accelerate drying and/or curing of coating material (202) as element material (13) passes through drying assembly (330).

Drum roll (334) is configured to manipulate element material (13) through drying chamber (332). As described above, drying chamber (332) the air and/or conditions within drying chamber (332) are generally manipulated to accelerate drying and/or curing of coating material (202). To increase the amount of exposure of coating material (202) to the conditions of drying chamber (332), drum roll (334) defines an axial length that is configured to accommodate several turns of element material (13) in a helical configuration. Although not shown, it should be understood that in some examples drum roll (334) can include channels, protrusions, and/or other geometric features to direct element material (13) along the helical path shown in FIG. 3.

At least a portion of drum roll (334) is in mechanical communication with a motor (336). Motor (336) is configured to drive rotation of drum roll (334) to thereby "pull" element material (13) through drying assembly (330). In some example, the rotation generated by motor (336) may also be sufficient to "pull" element material (13) from raw material spool (310) through spray assembly (320) and into drying assembly (330).

Coat spool (350) is positioned next to drying assembly (330). Coat spool (350) is generally configured to rotate to accumulate coated element material (13) after element material passes through drying assembly (330). To assist with such rotation, coat spool (350) is mechanically coupled to a motor (352), which provides rotation of coat spool (350). In some examples, motor (352) provides sufficient power to coat spool (350) to merely "pull" element material (13) from drying assembly (330) to coat spool (350). However, in other examples, motor (352) provides sufficient power to "pull" element material (13) entirely through coating system (300). In such versions, drum roll (334) may act as an idler and motor (336) may be omitted.

In an exemplary method of coating element material (13) using coating system (300), element material (13) begins at raw material spool (310). It should be understood that at this stage a predetermined amount of element material (13) is spooled around raw material spool (310) to continuously provide element material (13) as raw material spool (310) is rotated. To drive element material (13) through the components of coating system (300), coat spool (350) is positioned at an end of coating system (300), opposite of raw material spool (310). Motor (352) thus drives rotation of coat spool (350) to "pull" element material (13) from raw material spool (310) to coat spool (350).

As element material (13) progresses between raw material spool (310) and coat spool (350), element material (13) is first directed through spray assembly (320). During this stage, sprayers (322, 324) spray coating material (202) onto the outer surface of element material (13), thereby fully coating the exterior of element material (13) with coating material (202). Prior to beginning the coating process, it should be understood that coating material (202) may be manufactured in accordance with the specifications above and then added to dip tank (220) initially or on a continuous basis.

Once element material (13) has been coated via spray assembly (320), element material (13) is next received in drying assembly (330) to initiate the drying process. During the drying process, element material (13) winds around drum roll (334) in a helical configuration. Drum roll (334) is rotated via motor (336) to progressively drive element material (13) lower on drum roll (334). This process exposes element material (13) to the conditions of drying chamber (332), which accelerates the drying and/or curing of coating material (202) on element material (13). In the present example, the process of moving element material (13) from the top of drum roll (334) to the bottom of drum roll (334) takes between about 30 minutes to about 3 hours (e.g., exposure time). However, in other examples the speed of drum roll (334) or the physical dimensions of drum roll (334) can be varied to increase or decrease the particular amount of exposure time.

As described above, exposure to the conditions within drying chamber (332) accelerates drying and/or curing of coating material (202) on element material (13). In the present example, this includes heating the atmospheric temperature of drying chamber (332) to approximately 100° C. In other examples, this can also include increasing the movement of air within drying chamber (332) to a predetermined velocity. In still other examples, coating material (202) may not be completely responsive to heat. In such examples, various alternative drying and/or curing mechanisms may be used. For instance, in some examples coating material (202) is cured by certain wavelengths of light. Thus, coating material (202) and element material (13) can also be exposed to certain predetermined wavelengths of light when disposed within drying chamber (332).

After element material (13) progresses to the bottom of drum roll (334), element material (13) travels to coat spool (350). Once at coat spool (350), element material (13) is wound around coat spool (350) for storage until all element material (13) has progressed from raw material spool (310) to coat spool (350).

After element material (13) has progressed entirely from raw material spool (310) to coat spool (350), element material (13) is entirely coated with coating material (202). Element material (13) is next used to prepare a marker element similar to marker element (12) described above. The particular marker element formed depends in part on the initial shape of element material (13). For instance, if element material (13) is in wire form, element material (13) can be cut into a plurality of segments of a predetermined length. Each segment is then shaped to form a predetermined marker element geometry such as a spring shape. Alternatively, if element material (13) is in a strip form, element material (13) can be cut into a plurality of blanks of a predetermined shape (e.g., bow tie). Each blank can then be shaped into a final configuration as desired.

Regardless of the particular formation of marker material (13) into a marker element, each completed marker element is next formed into a completed marker similar to marker (100) described above. As described above, the marker element may be used alone as the marker (e.g., a bare marker) or suspended in a carrier similar to carrier (120) described above. Regardless, the final marker can be next used for marking purposes by inserting the completed marker into tissue via a marker delivery device or other suitable devices and/or methods as will be described in greater detail below.

C. Exemplary Continuous Extrusion Coating System

Figure 4:
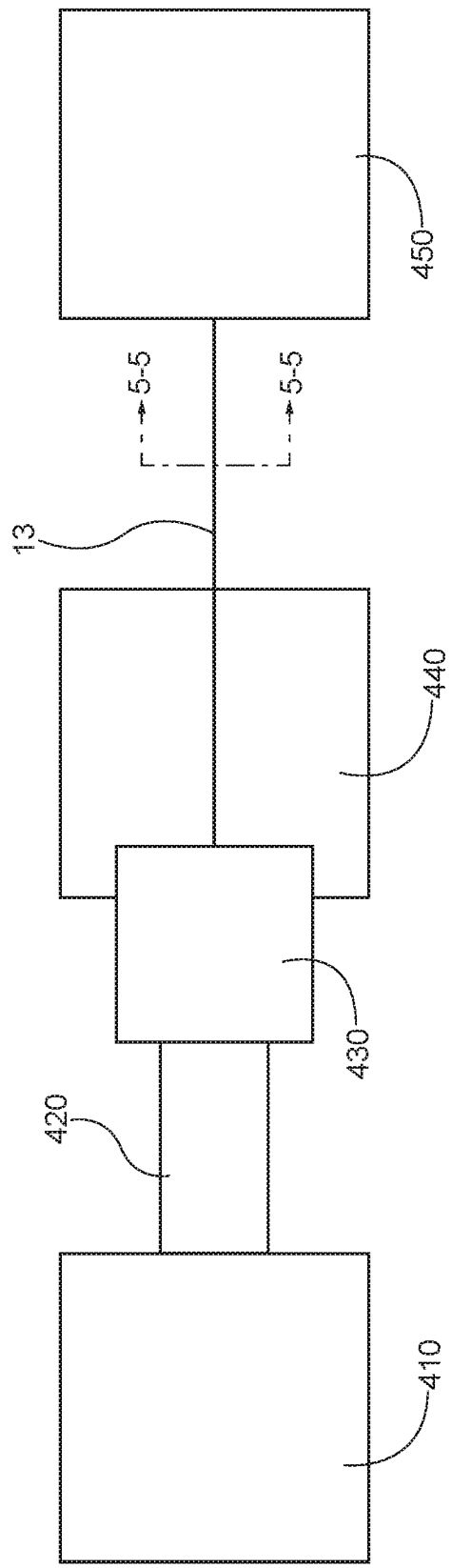
FIG. 4 depicts a side elevational view of an exemplary continuous extrusion coating system for use in coating the element material of FIG. 2.

FIG. 4 shows an exemplary continuous extrusion coating system (400) for use in an operation to coat element material (13) with coating material (202). Coating system (400) includes a material hopper (410), a transport tube (420), a die (430), a material combiner (440), and a drying assembly (450). As will be described in greater detail below, coating assembly (400) is generally configured to extract molten element material (13) into a predetermined shape and then fill and coat the predetermined shape of element material (13) with coating material (202).

Material hopper (410) is generally configured to contain element material (13) in a molten or liquid state. It should be understood that material hopper (410) may take on a variety of shapes and sizes. For instance, in some examples material hopper (410) is a hollow cylindrical container. In other examples, material hopper (410) is a rectangular or square container. Of course, any other suitable container shape may be used as will be apparent to those of ordinary skill in the art.

As described above, element material (13) can include a variety of materials. Accordingly, it should be understood that material hopper (410) can have a variety of thermodynamic properties that corresponds to the particular material used for element material (13). For instance, in the present example it is contemplated that coating system (400) may be used with a polymeric material as element material (13). Thus, material hopper (410) can be correspondingly configured to contain polymeric material while in a liquid state. Pursuant to this, material hopper (410) can include insulation, interior coatings, heaters, and/or etc. to contain element material (13) while also maintaining element material (13) in a liquid state. Similarly, in other examples, element material (13) can comprise metallic materials. In such examples, material hopper (410) can include corresponding materials to contain molten metal such as insulation, refractory materials, internal coatings, heaters, and/or etc. Of course, various alternative configurations for material hopper will be apparent to those of ordinary skill in the art in view of the teachings herein.

Transport tube (420) is generally configured to transport element material (13) from material hopper (410) to die (430). As with material hopper (410) described above, it should be understood that transport tube (420) generally includes materials that reflect the particular material used for element material (13). Additionally, transport tube (420) is generally configured to withstand relatively high pressures as element material (13) is forced through die (430) via transport tube (420).

Although transport tube (420) is shown schematically in the present example, it should be understood that transport tube (420) may take on a variety of shapes and/or sizes. For instance, in some examples transport tube (420) is a generally tubular structure. Alternatively, in some examples, transport tube (420) comprises a generally hollow square or rectangular structure. Of course, a variety of other shapes and/or sizes for transport tube (420) may be used as will be apparent to those of ordinary skill in the art in view of the teachings herein.

Die (430) is generally configured to manipulate element material (13) into a predetermined shape as element material (13) is forced through die (430) from transport tube (420). In the present example, die (430) is configured to manipulate element material (13) into a generally tubular shape. Although not shown, it should be understood that die (430) may include a mandrel or other similar structure to assist with formation of element material (13) into the generally tubular shape. In other examples, die (430) is configured to form element material (13) into a variety of other shapes. For instance, in some examples die (430) is configured to form element material (13) into a cylindrical solid rod shape or any other shape as will be apparent to those of ordinary skill in the art in view of the teachings herein.

Figure 5:
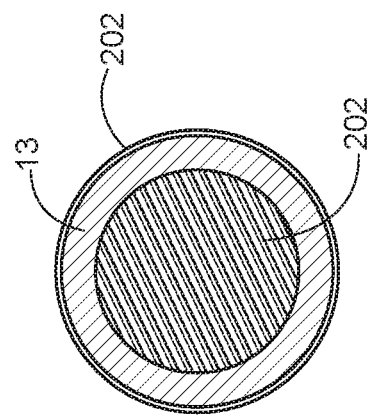
FIG. 5 depicts a front cross-sectional view of the element material formed using the system of FIG. 4, the cross-section taken along line 5-5 of FIG. 4.

Material combiner (440) is disposed adjacent to die (430). Material combiner (440) is generally configured to coat and/or fill element material (13) as element material (13) is extruded through die (430). For instance, as shown in FIG. 5, element material (13) is manipulated by die (430) into a generally tubular shape. Once element material (13) is manipulated into this shape, material combiner (440) is configured to coat the exterior of element material (13) with coating material (202). In addition, material combiner (440) is configured to fill the interior of element material (13) to provide a solid core of coating material (202).

A variety of structures may be used to provide a coating of coating material (202) onto the exterior of element material (13). For instance, in some examples material combiner (440) can include a material reservoir such that element material (13) may be entirely submerged into a predetermined quantity of coating material (202). Alternatively, in other examples material combiner (440) can include one or more sprayers to spray coating material (202) onto the exterior of element material (13). In still other examples, a variety of alternative structures for coating the exterior of element material (13) may be used as will be apparent to those of ordinary skill in the art in view of the teachings herein.

A variety of structures may also be used to fill the interior of element material (13) with coating material (202). For instance, in some examples material combiner (440) can include a rigid tube disposed adjacent to die (430). This tube may protrude into the interior of the shape formed by element material (13) while element material (13) is still in a plastic or semi-solid state. Thus, a slit may be formed in the generally tubular shape of element material (13) as element material (13) is extruded from die (430). This slit may later be sealed or closed as element material (13) solidifies. However, while the tube of material combiner (440) is disposed within element material (13), the tube may be used to inject coating material (202) into the interior of the generally tubular shape of element material (13). In other examples, material combiner (440) fills the interior of element material (13) in accordance with at least some of the teachings of U.S. Pat. No. 8,109,913, entitled "Coiled Wire for the Controlled Release of Drugs to the Eye," issued on Feb. 7, 2012, the teachings of which are incorporated by reference herein. In still other examples, a variety of alternative structures of injecting coating material (202) into the interior of element material (13) may be used as will be apparent to those of ordinary skill the art in view of the teachings herein.

FIG. 4 shows drying assembly (450) schematically. Although not shown, it should be understood that in some examples drying assembly (450) may be configured similarly to drying assemblies (230, 330) described above. For instance, in some examples drying assembly (450) comprises a drying chamber (not shown) and a cylindrical drum roll (not shown). As with drying chambers (232, 332) described above, the drying chamber is configured to accommodate the drum roll such that the drum roll may freely rotate within the drying chamber. Additionally, in some examples the drying chamber is in communication with blowers, heaters, light emitters, or other devices configured to manipulate the conditions within the drying chamber. As will be described in greater detail below, the air or other conditions within the drying chamber are generally manipulated to accelerate drying and/or curing of coating material (202) as element material (13) passes through the drying assembly.

Like with drum rolls (224, 334) described above, the drum roll of drying assembly (450) is configured to manipulate element material (13) through the drying chamber. As described above, the drying chamber the air and/or conditions within the drying chamber are generally manipulated to accelerate drying and/or curing of coating material (202). To increase the amount of exposure of coating material (202) to the conditions of the drying chamber, the drum roll defines an axial length that is configured to accommodate several turns of element material (13) in a helical configuration.

Like with drying assemblies (230, 330), in at least some examples of drying assembly (450), a motor may be used to drive various components of drying assembly (450). For instance, in the example described above, at least a portion of the drum roll is in mechanical communication with a motor (not shown). The motor is configured to drive rotation of the drum roll to thereby "pull" element material (13) through drying assembly (450).

In an exemplary use of coating system (400), element material (13) begins within material hopper (410). During this stage, element material (13) is in a molten or liquid form. In this form, element material (13) is transported through transport tube (420). To transport element material (13) through transport tube (420), material hopper (410) may include a hydraulic press, a fluid pump, a piston, and/or other structural elements configured to force element material (13) through transport tube (420). Alternatively, in some examples material hopper (410) may merely be positioned above other components of coating system (400) to feed element material (13) using gravity.

Regardless of how element material (13) is forced into transport tube (420), transport tube (420) is used to transport element material (13) into die (430). At this stage, element material (13) remains in a molten or liquid state. However, in some examples element material (13) may at least partially solidify within transport tube (420) such that the viscosity of element material (13) may increase as element material (13) is transported from material hopper (410) to die (430).

Once element material (13) is received within die (430), various geometric features of die (430) manipulate element material (13) into a predetermined shape. As described above, die (430) of the present example is configured to manipulate element material (13) into a generally tubular shape, although a variety of other shapes may be used. In the present example, element material (13) flows continuously through die (430) to provide a constant flow of element material (13) in the extruded generally tubular configuration.

As element material (13) is driven past die (430), element material (13) begins to solidify. During this solidification process, material combiner (440) engages the solidifying element material (13) to coat the exterior of element material (13) while simultaneously filling the interior of element material (13) with coating material (202). As described above, the exterior of element material (13) can be coated with a sprayer, dip bath, and/or other structural elements associated with material combiner (440) to provide a coating of coating material (202) on the exterior of element material (13). During this coating process, or at a substantially similar time, the interior of element material (13) is also filled with coating material (202). In the present example, a rigid tube is used to inject coating material (202) into the tubular structure of element material (13) during solidification. As described above, access to the interior of element material (13) can be achieved through a slit within the surface of element material (13). In examples using a slit in the exterior of element material (13), the curing process may also include manipulating element material (13) to seal and/or close the slit after element material (13) is extruded past the tube associated with material combiner (440).

After element material (13) passes through material combiner (440), the continuous extrusion process pushes element material (13) away from material combiner (440) and into drying assembly (450). At this stage, element material

(13) is subjected to a variety of conditions such as heat, light, and/or etc. to accelerate the curing and/or drying of coating material (202).

Once coating material (202) has sufficiently dried via drying assembly (450), the coated element material (13) may be spooled for later use. Alternatively, element material (13) may be directly cut and/or shaped into a final marker element (12). Regardless of when element material (13) is finally used to form a marker element (12), element material (13) is next used to prepare a marker element similar to marker element (12) described above. The particular marker element formed depends in part on the initial shape of element material (13). For instance, if element material (13) is in tubular form as described above, element material (13) can be cut into a plurality of segments of a predetermined length. Each segment is then shaped to form a predetermined marker element geometry such as a spring shape. Alternatively, if element material (13) is in a strip form, element material (13) can be cut into a plurality of blanks of a predetermined shape (e.g., bow tie). Each blank can then be shaped into a final configuration as desired.

Regardless of the particular formation of marker material (13) into a marker element, each completed marker element is next formed into a completed marker similar to marker (100) described above. As described above, the marker element may be used alone as the marker (e.g., a bare marker) or suspended in a carrier similar to carrier (120) described above. Regardless, the final marker can be next used for marking purposes by inserting the completed marker into tissue via a marker delivery device or other suitable devices and/or methods as will be described in greater detail below.

D. Exemplary Continuous Marker Element Forming and Coating System

FIGS. 6-8 show an exemplary marker element formation and coating system (500). Formation and coating system (500) generally includes two stages—an element formation stage (510) and an element coating stage (550). Two examples of an element formation stage are shown in FIGS. 6 and 7, respectively. For instance, FIG. 6 shows an exemplary laser formation stage (512). As can be seen, laser formation stage (512) includes a laser emitter (514). Laser emitter (514) is generally configured to emit a focused laser beam of sufficient power to cut through element material (13).

Although not shown, it should be understood that in some examples laser emitter (514) is coupled to a computer numerical control (CNC) machine to direct laser emitter (514) along a predetermined path. In other examples laser emitter (514) is spatially fixed while the laser beam itself is moved along a predetermined path via optics. Regardless, as will be described in greater detail below, it should be understood that laser emitter (514) is generally configured to cut element material (13) into a desired shape to form an element blank (15) that may be later used to form a marker element similar to marker element (12).

A stamp formation stage (520) is shown in FIG. 7. As can be seen, stamp formation stage (520) includes a press (522). Press (522) is generally configured to move vertically up and down as indicated by arrows. This action drives press (522) into element material (13), which causes press (522) to penetrate element material (13) in a predetermined pattern. Although not shown, it should be understood that in the present examples press (522) includes a die or other geometric feature that includes the predetermined pattern that is cut into element material (13). As will be described in greater detail below, this predetermined patter results in an element blank (15) being cut out of element material (15).

Although not shown, it should be understood that in some examples press (522) is coupled to a CNC machine as similarity described above in connection with laser emitter (514). Such a CNC machine may be configured to move press (522) between a plurality of predetermined locations to permit press (522) to cut element blanks (15) at different locations relative to element material (13). Alternatively, in some examples press (522) is merely fixed relative to a plane defined by element material (13) such that press (522) merely moves up and down perpendicularly relative to element material (13).

Regardless of whether system (500) is implemented with laser formation stage (512) or stamp formation stage (520), either implementation may be used in connection with element coating stage (550) shown in FIG. 8. Element coatings stage (550) is generally configured to coat a plurality of element blanks (15) after each blank (15) has been cut using either laser formation stage (512), stamp formation stage (520), or some combination thereof. Element coating stage (550) includes a conveyer (552), one or more sprayers (560), and a drying assembly (570). Conveyer (552) includes a belt (554), which is configured to support and transport a plurality of element blanks (15). Belt (554) is generally formed of a screen, wire, mesh, or perforated material. As will be understood, belt (554) is generally configured to support each element blank (15), while also leaving a substantial surface area of each element blank (15) exposed for the purposes of coating. Thus, belt (554) includes a plurality of openings that are sized sufficiently small to prevent element blanks (15) from falling through. By way of example only, suitable openings sizes can be between about 50 to about 150 microns.

Each sprayer (560) is configured to spray coating material (202) onto each element blank (15) to substantially coat each element blank (15) with coating material (202). In the present configuration, element coating stage (550) includes two sprayers (560) oriented in opposite directions. In this configuration, one sprayer (560) is configured to spray the underside of each element blank (15), while another sprayer (560) is configured to spray the top-side of each element blank (15). Although the present configuration is shown as using two sprayers (560), it should be understood that in other examples any suitable number of sprayers (560) may be used. In addition, or in the alternative, in other examples sprayers (560) may be oriented at any desired orientation relative to belt (554) as will be apparent to those of ordinary skill in the art in view of the teachings herein.

Drying assembly (570) is shown schematically as being adjacent to conveyer (552) such that belt (554) extends into drying assembly (570). As similarly described above with respect to drying assemblies (230, 330, 450), drying assembly (570) includes a drying chamber (not shown). As similarly described above, the drying chamber of drying assembly (570) may be in communication with a plurality of features configured to accelerate curing and/or drying of coating material (202). By way of example only, the drying chamber of drying assembly (570) may be in communication with blowers, heaters, lights, and/or etc.

Unlike drying assemblies (230, 330, 450) described above, drying assembly (570) generally omits a drum roll or other similar feature. Instead, conveyer (552) is used to move element blanks (15) through the drying chamber of drying assembly (570). As will be described in greater detail below, conveyer (552) is generally configured to move element blanks (15) through drying assembly (570) to provide sufficient time for coating material to sufficiently cure or dry under the conditions within the drying chamber. By way of example only, a sufficient time for exposure can be about 30 minutes to about two hours in a temperature of about 100° C.

In an exemplary use of formation and coating system (500), a roll of element material (13) in sheet form is obtained. When element material (13) is in sheet form, element material (13) has a width that is generally several times greater than the final transverse width of marker element (12). The thickness of element material (13) is generally at or near the final thickness of marker element (12). In this form, a plurality of element blanks (15) can be cut from the sheet of element material (13) via laser formation stage (512) or stamp formation stage (520).

To begin cutting element blanks (15), an end of element material (13) is loaded into a desired formation stage (512, 520). Once loaded, element material (13) is continuously fed into the desired formation stage (512, 520) via rollers, motors, conveyers, and/or etc. As element material (13) is fed into the desired formation stage (512, 520), element blanks (15) are cut using either laser emitter (514) or press (522), depending on the particular formation stage (512, 520) used.

As element blanks (15) are cut, element blanks (15) may be collected in a basket, conveyer, or other container/transporter. Each cut element blank (15) is then transported to element coating stage (550).

Once element blanks (15) have been transported to element coating stage (550), each element blank (15) is laid or placed on conveyer (552) in a spaced apart arrangement. Conveyer (552) moves element blanks (15) in a linear fashion through element coatings stage (550). This results in the exterior surface of each element blank (15) being sprayed with coating material (202) via one or more sprayers (560).

Once element blanks (15) have been sprayed with sprayers (560), conveyer (552) continues to transport element blanks (15) until element blanks (15) are transported into the drying chamber of drying assembly (570). This exposes element blanks (15) to the internal conditions of the drying chamber. As described above, the present example uses a temperature of about 100° C. to accelerate the curing/drying time of coating material (202). Correspondingly, conveyer (552) moves at a rate sufficient to expose coating material (202) to the internal conditions of the drying chamber for a time of amount 30 minutes to about 2 hours.

Once element blanks (15) have traveled through drying assembly (570), element blanks (15) are collected for further processing. In some examples, further processing may include bending each element blank (15) into a final shape. Alternatively, further processing may be minimal and each element blank (15) may be a final marker element similar to marker element (12) immediately after drying.

Regardless of the particular final processing of element blanks (15), each completed marker element is next formed into a completed marker similar to marker (100) described above. As described above, the marker element may be used alone as the marker (e.g., a bare marker) or suspended in a carrier similar to carrier (120) described above. Regardless, the final marker can be next used for marking purposes by inserting the completed marker into tissue via a marker delivery device or other suitable devices and/or methods as will be described in greater detail below.

III. EXEMPLARY METHOD FOR DEPOSITING A MARKER OR MARKER ELEMENT INTO TISSUE

Figure 9:
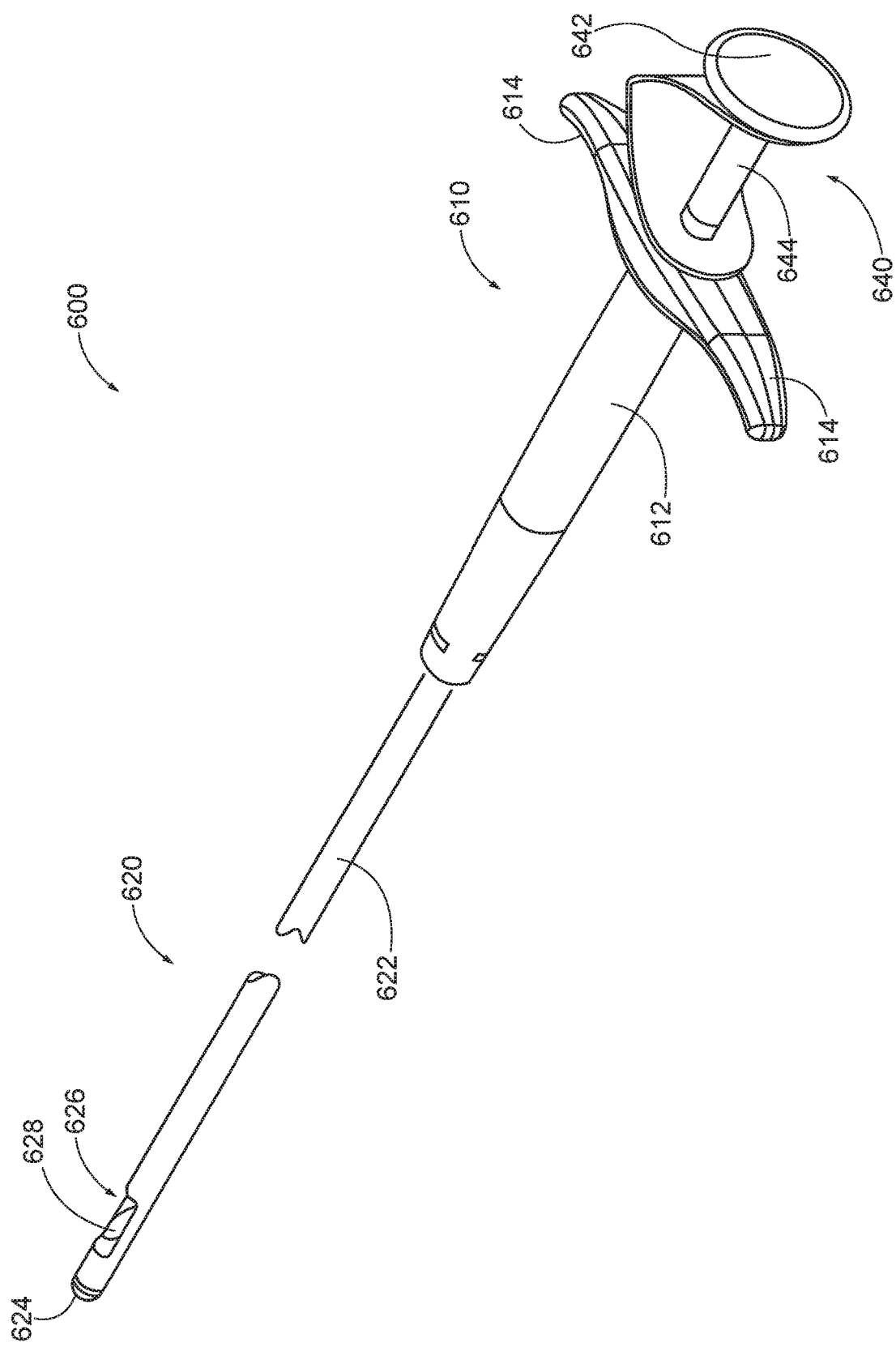
FIG. 9 depicts a perspective view of an exemplary marker delivery device that may be readily used with any one or more of the systems of FIGS. 2, 3, 4, and 6.

FIG. 9 shows an exemplary marker delivery device (600) that can be used in connection with marker (100) described above after formation of marker element (12) using any one or more of systems (200, 300, 400, 500) described above. Marker delivery device (600) generally includes a handle assembly (610), a delivery catheter (620), and a push rod (640). Handle assembly (610) is generally configured to provide a grip for an operator to readily manipulate marker delivery device (600). In the present example, handle assembly (610) includes a body (612) and a pair of grip arms (614) extending outwardly from body (612). Each grip arm (614) is generally shaped to receive one or more fingers of an operator such that operator may readily manipulate marker delivery device (600).

Delivery catheter (620) extends distally from body (612) of handle assembly (610). Delivery catheter (620) includes an elongate cannula (622) that is distally closed by a blunt distal portion (624). Proximally of distal portion (624), cannula (622) defines a lateral aperture (626). As will be described in greater detail below, lateral aperture (626) is generally configured to permit marker (100) and/or marker element (12) to be ejected from delivery catheter (620).

Delivery catheter (620) further includes a ramp portion (628) disposed within cannula (622) adjacently relative to lateral aperture (626). Ramp portion (628) is generally configured to hold marker (100) and/or marker element (12) within delivery catheter (620), thereby preventing inadvertent ejection of marker (100) and/or marker element (12). As will be described in greater detail below, ramp portion (628) is also generally configured to eject marker (100) and/or marker element (12) laterally out of lateral aperture (626) when an operator desires to deliver marker (100) and/or marker element (12) to a biopsy site.

Push rod (640) is generally configured to manipulate marker (100) and/or marker element (12) to selectively eject marker (100) and/or marker element (12). Push rod (640) includes a button portion (642) and an elongate rod portion (644). Button portion (642) is disposed proximally of handle assembly (610) such that button portion (642) is readily accessible to an operator when gripping marker delivery device (600) via grip arms (614). As will be understood, button portion (642) is generally configured to be manipulated by an operator to drive rod portion (644) distally and thereby eject marker (100) and/or marker element (12) from marker delivery device (600).

Rod portion (644) extends distally from button portion (642). In particular, rod portion (644) extends distally into handle assembly (610). Although not shown, it should be understood that rod portion (644) additionally extends through handle assembly (610) and into cannula (622) of delivery catheter (620). This permits a distal portion of rod portion (644) to be positioned adjacent to lateral aperture (626) to thereby drive marker (100) and/or marker element (12) out of lateral aperture (626).

In an exemplary use, marker element (12) is formed from marker material (13) using the methods described above in connection with any one or more of systems (200, 300, 400, 500). After formation of marker element (12) it should be understood that marker element (12) is coated with coating material (202) such that marker element (12) will be readily visible under ultrasonic visualization via the microspheres disposed within coating material (202). The coated marker element (12) can next be used without any additional coating or carrier similar to carrier (120) described above (e.g., a "bare" marker). Alternatively, in some examples, marker element (12) undergoes additional steps to dispose marker element (12) within carrier (120) to form marker (100).

Regardless of whether marker element (12) is used in the bare condition or is disposed within carrier (120), the completed marker (100) is next loaded into marker delivery device (600). In the present example, marker (100) may be loaded into marker delivery device (600) through lateral aperture (626) of delivery catheter (620). After loading, marker (100) is held in position by ramp portion (628) and rod portion (644) of push rod (640) is disposed proximally of marker (100).

Figure 10:
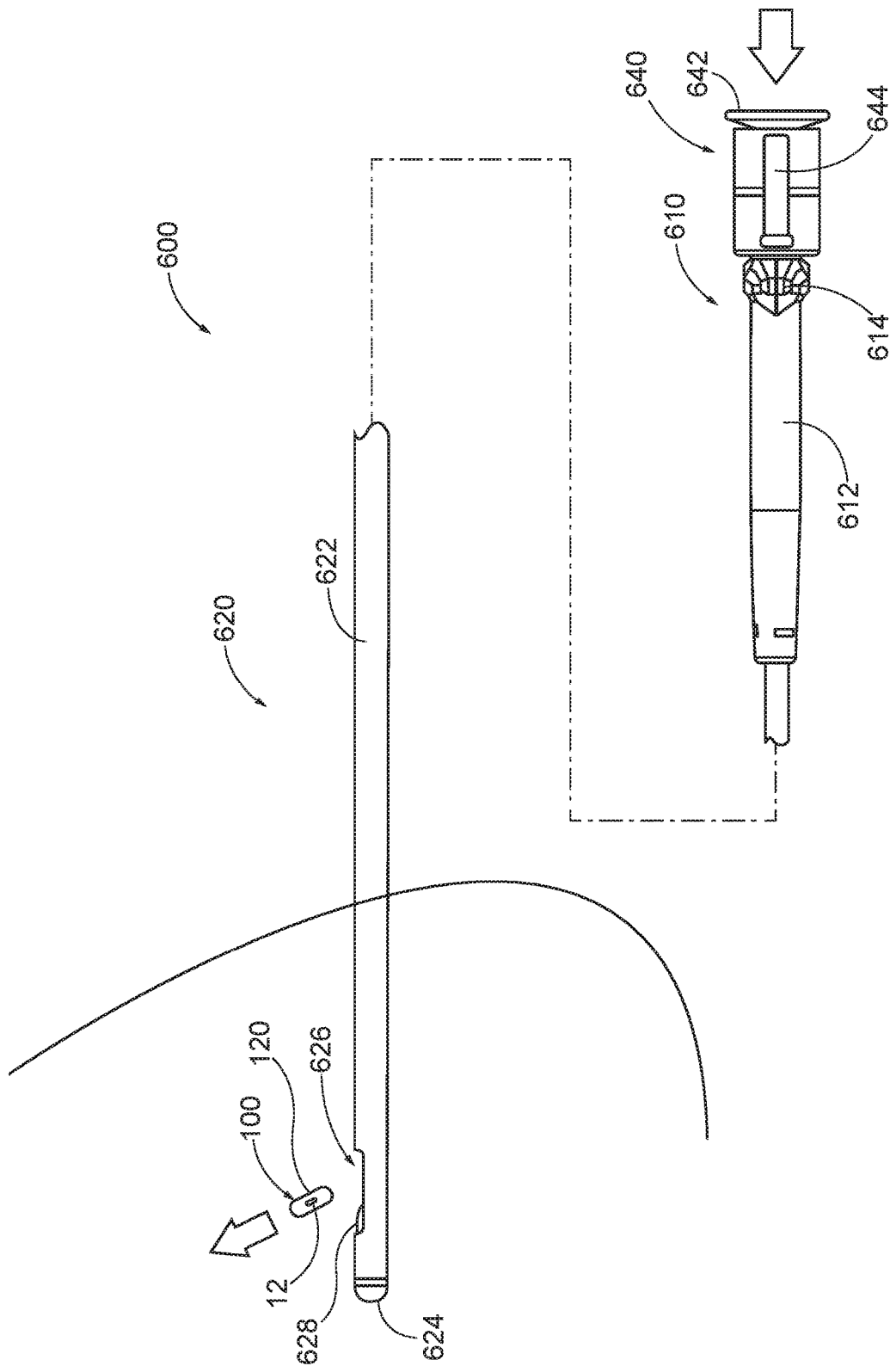
FIG. 10 depicts a side elevational view of the marker delivery device of FIG. 9 being used to deploy a biopsy site marker at a biopsy site.

Once marker (100) is loaded within marker delivery device (600), marker delivery device (600) is ready for insertion into a patient to deploy marker (100) at a biopsy site. As can be seen in FIG. 10, the deployment process starts with insertion of delivery catheter (620) into a patient. Although delivery catheter (620) is shown in the present example as being inserted directly into a patient, it should be understood that in other examples delivery catheter (620) can be inserted into a patient indirectly via other instruments. For instance, in some examples a biopsy device can be used for insertion of delivery catheter (620). In such examples, the biopsy device can include various access ports to permit delivery catheter (620) to be inserted into a needle of the biopsy device. The needle of the biopsy device is then used for insertion of delivery catheter (620) and subsequent delivery of marker (100).

Once delivery catheter (620) is disposed within a patient as desired, an operator may deploy marker (100) at the biopsy site. As seen in FIG. 10, an operator can deploy marker (100) by pressing button portion (642) of push rod (640). This causes rod portion (644) of push rod (640) to advance within cannula (622) of delivery catheter (620). The distal portion of rod portion (644) then engages the proximal end of marker (100). This forces marker (100) up ramp portion (628), which ejects marker (100) out of lateral aperture (626) and into the biopsy site. Although FIG. 10 shows marker (100) as including a carrier (120) and marker element (12) configuration, it should be understood that marker delivery device (600) may be readily used to deploy a marker (100) including only marker element (12) using the same procedures described herein.

After deployment of marker (100), an operator may confirm the positioning of marker (100) using ultrasonic visualization. In the present example, ultrasonic visualization is enhanced via coating material (202) disposed on the exterior of marker element (12) due to the numerous reflecting surfaces of the microspheres of coating material (202). After the positioning of marker (100) is confirmed, marker delivery device (600) can be removed and the patient can be sealed using conventional methods. In subsequent follow-up procedures, marker (100) can be further visualized using ultrasonic visualization enhanced by the numerous reflecting surfaces of microspheres of coating material (202) disposed on the surface of marker element (12). In examples where marker element (12) is used along with a carrier (120), this enhanced visualization persists even after carrier (120) has absorbed into the patient.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A marker delivery device comprising: a delivery catheter adapted to be inserted into a biopsy site, the delivery catheter having a discharge opening; a marker having a coating layer disposed on the surface of a core, the coating layer containing an adhesive with a plurality of microbubbles configured to enhance visibility under ultrasound imaging, the marker being positioned inside the delivery catheter near the discharge opening; a push rod positioned within the delivery catheter and adapted to deploy the marker from the delivery catheter into the biopsy site.

Example 2

The marker delivery device of Example 1, wherein the marker is enclosed in a bioabsorbable carrier.

Example 3

The marker delivery device of Example 1, wherein the marker is enclosed in a bioabsorbable carrier whose volume is configured to expand upon contact with liquid inside the biopsy site.

Example 4

The marker delivery device of any one or more of Examples 1 through 3, wherein the marker includes a metallic marker ceramic marker or plastic marker.

Example 5

The marker delivery device of any one or more of Examples 1 through 4, further comprising a carrier, wherein the marker is wrapped around the carrier.

Example 6

A method of manufacturing a marker delivery device comprising: selecting gas-filled microparticles whose average size is less than 500 microns; mixing the selected microparticles with an adhesive solution to create a coating solution; applying the coating solution to a biopsy site marker; drying the coated marker; positioning the dried marker in a delivery catheter near a discharge opening for deployment into the biopsy site by a push rod positioned inside the delivery catheter.

Example 7

A system for enhancing element material for use in forming a marker element, the system comprising: one or more sprayers, wherein the one or more sprayers are configured to coat the element material with a coating material including a plurality of microspheres; one or more material manipulators wherein the one or more material manipulators are configured to reposition the element material; and a drying assembly configured to accelerate drying of the coating material.

Example 8

The system of Example 7, wherein the one or more material manipulators includes a conveyer, wherein the conveyer includes a belt comprising a plurality of openings.

Example 9

The system of any one or more of Examples 7 through 8, further comprising a material cutting portion, wherein the material cutting portion is configured to cut the element material into a plurality of element blanks, wherein the one or more sprayers are configured to coat each element blank of the plurality of element blanks.

Example 10

The system of Example 9, wherein the material cutting portion includes at least one or more of a laser cutter or a stamper.

Example 11

The system of any one or more of Examples 7 through 10, wherein the drying assembly includes a drying chamber, wherein the drying chamber is configured to define internal conditions that are configured to accelerate drying of the coating material.

Example 12

The system of Example 11, wherein the drying chamber includes a heating element, wherein the heating element is configured to heat the internal conditions of the drying chamber to a predetermined temperature.

Example 13

A system for enhancing an element material for use in forming a marker element, the system comprising: a coating element, wherein the coating element configured to coat the element material with a coating material including a plurality of microspheres; one or more material manipulators wherein the one or more material manipulators are configured to reposition the element material; and a drying assembly configured to accelerate drying of the coating material.

Example 14

The system of Example 13, wherein the coating element includes a reservoir, wherein the reservoir is filled with a quantity of the coating material.

Example 15

The system of Example 14, wherein at least a portion of the element material is disposed within the reservoir to coat the at least a portion of the element material with the coating material.

Example 16

The system of Examples 13 through 15, wherein the drying assembly includes a drum roll, wherein the drum roll is configured to receive at least a portion of the element material around the drum roll in a helical pattern.

Example 17

A system for enhancing element material for use in forming a marker element, the system comprising: a material hopper, wherein the material hopper is configured to extrude the element material through a die; a material combiner configured to coat the extruded element material with a coating material, the coating material including a plurality of microspheres; and a drying assembly configured to accelerate drying of the coating material.

Example 18

The system of Example 17, wherein the die is configured to manipulate at least a portion of the element material into a tubular shape.

Example 19

The system of Example 18, wherein the material combiner is configured to fill the tubular shape of the at least a portion of the element material with the coating material.

Example 20

The system of any one or more of Examples 17 through 19, wherein the drying assembly is configured to expose at least a portion of the element material to a temperature of about 100° C. for about 30 minutes to 2 hours.

V. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of manufacturing a marker delivery device comprising:
    coating a biopsy site marker with microspheres, the step of coating including coating a marker material and forming the coated marker material into a predetermined shape of the biopsy site marker;
    drying the coated marker, the coating of the microspheres enhancing ultrasound visibility of the marker;
    positioning the marker inside a delivery catheter near its discharge opening; and
    positioning a push rod within the delivery catheter, the push rod adapted to deploy the marker from the delivery catheter into the biopsy site.

2. The method of claim 1, further comprising the step of enclosing the marker within a bioabsorbable carrier.

3. The method of claim 1, further comprising the step of enclosing the marker within a bioabsorbable carrier whose volume is configured to expand upon contact with liquid inside the biopsy site.

4. The method of claim 1, the marker including a metallic marker, ceramic marker, or plastic marker.

5. The method of claim 1, further comprising the step of wrapping the marker around a bioabsorbable carrier.

6. The method of claim 1, the plurality of microbubbles including gas-filled microparticles.

7. The method of claim 1, the plurality of microbubbles including gas-filled microparticles whose average size is less than 500 microns.

8. The method of claim 1, the plurality of microbubbles having an average size of less than 500 microns.

9. The method of claim 1, wherein the plurality of microbubbles having an average size of between 1 and 250 microns.

10. A method of manufacturing a marker delivery device comprising:
    selecting gas-filled microparticles whose average size is less than 500 microns;
    mixing the selected microparticles with an adhesive to create a coating mixture;
    applying the coating mixture to a portion of an elongate marker material;
    drying the marker element coating mixture onto the elongate marker material;
    cutting a marker element blank from the elongate marker material with at least a portion of the marker element blank being coated;
    forming the marker element blank into a marker element:
    enclosing the marker element in a bioabsorbable carrier to form a biopsy site marker; and
    positioning the biopsy site marker in a delivery catheter near a discharge opening for deployment into the biopsy site by a push rod positioned inside the delivery catheter.

11. The method of claim 10, the step of enclosing the dried marker element including enclosing the dried marker element within a hydrogel material.

12. The method of claim 10, the step of manipulating a portion of the marker material into a tubular shape being performed using a die in a continuous process.

13. A method of manufacturing a marker delivery device comprising:
    (a) coating a blank material with a coating material, the coating material including a plurality of microparticles whose average size is less than 500 microns;
    (b) cutting a portion of the coated blank material to form a marker element at least partially coated with the coating material;
    (c) inserting the marker element into a carrier to form a biopsy site marker, the carrier including a hydrogel material;
    (d) inserting the biopsy site marker into a delivery catheter through a lateral aperture device by the delivery catheter, the lateral aperture being proximate a push rod positioned inside the delivery catheter.

14. The method of claim 13, the blank material including a sheet material.

15. The method of claim 13, the step of coating the blank material includes drawing the coating material from a reservoir.

16. The method of claim 13, further comprising forming the marker element into a predetermined shape.

17. The method of claim 16, the step of forming the marker element into a predetermined shape including forming the marker element into a spring shape.

* * * * *

UNITED STATES PATENT AND TRADEMARK OFFICE
CERTIFICATE OF CORRECTION

| | |
|---|---|
| PATENT NO. | : 11,191,610 B2 |
| APPLICATION NO. | : 16/141077 |
| DATED | : December 7, 2021 |
| INVENTOR(S) | : Harry Ahn et al. |

It is certified that error appears in the above-identified patent and that said Letters Patent is hereby corrected as shown below:

In the Claims

Column 25, Claim 7, Line 27 reads "the plurality of microbubbles"; which should be deleted and replaced with "the plurality of microspheres"

Column 25, Claim 8, Line 30 reads "the plurality of microbubbles"; which should be deleted and replaced with "the plurality of microspheres"

Column 25, Claim 9, Lines 32 and 33 read "the plurality of microbubbles"; which should be deleted and replaced with "the plurality of microspheres"

Signed and Sealed this
Nineteenth Day of July, 2022

Katherine Kelly Vidal
*Director of the United States Patent and Trademark Office*